United States Patent [19]

Lapinet et al.

[11] 4,208,406
[45] Jun. 17, 1980

[54] COMPOSITION FOR THE TREATMENT AND PREVENTION OF SKIN, EYE AND MUCOSAL INFLAMMATION

[76] Inventors: Eugène Lapinet, 17, Galerie Vivienne, Paris, France, 75002; Georges Cehovic, 7, Résidence de la Vallée, Palaiseau, France, 92120; Théodore Posternak, 25, Rue de l'Athénée, Geneva, Switzerland, 1206

[21] Appl. No.: 815,653

[22] Filed: Jul. 14, 1977

[30] Foreign Application Priority Data

Jul. 15, 1976 [GB] United Kingdom ............... 29421/76
May 11, 1977 [GB] United Kingdom ............... 19678/77

[51] Int. Cl.$^2$ ..................... A61K 31/70; C07H 17/00
[52] U.S. Cl. ................................ 424/180; 536/24; 536/27; 536/28
[58] Field of Search .................... 536/27, 28; 424/180

[56] References Cited

U.S. PATENT DOCUMENTS 3,856,776  12/1974  Cehovic et al. ............... 536/27
3,860,706   1/1975  Ikeda et al. .................. 536/27

*Primary Examiner*—Johnnie R. Brown
*Assistant Examiner*—Blondel Hazel
*Attorney, Agent, or Firm*—Eyre, Mann, Lucas & Just

[57] ABSTRACT

Composition for treatment or prevention of skin, eye or mucosal inflammation in human and animals, especially but not exclusively by external topical application comprising an effective amount of a cyclic nucleotide derivative having the following structural formula:

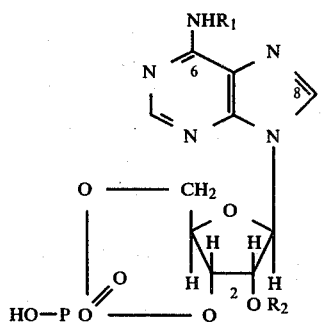

wherein $R_1$ and $R_2$, either are both a butyryl radical or one stands for a hydrogen atom and the other for a butyryl radical or both hydrogen atom; this compound may be used as such or in the form of any pharmaceutically acceptable salt of the same.

The compounds of the general formula are 3', 5' adenosine monophosphate of cAMP derivatives.

4 Claims, No Drawings

COMPOSITION FOR THE TREATMENT AND PREVENTION OF SKIN, EYE AND MUCOSAL INFLAMMATION

FIELD OF THE INVENTION

The present invention generally relates to a method for preventing or curing irritation and inflammation of the skin, eye and mucosa of humans and animals.

BACKGROUND OF THE PRIOR ART

Cyclic 3', 5' adenosine monophosphate (cyclic AMP) appears to be involved in the regulation of function and metabolism of a large variety of tissues and has been identified as a "second messenger" in the concept of hormone action by Sutherland (Harvey Lectures, 57, 17, 1962; Circulation, 37, 279 (1968)).

It was demonstrated that certain hormones and mediations of inflammation act in vivo to regulate the character and intensity of inflammatory and immune responses, this regulation is mediated by a general inhibitory action of cyclic AMP. (L.M. Lichtenstein, "Cyclic AMP, Cell growth and the Immune response", Springer Verlay, New York, p. 147, 1974).

More recently it was reported that intracellular level of cyclic AMP can be very reduced during imflammation by reduction of adenyl cyclage activity or increased phosphodiesterases action. (F. Marks, Cancer Res. 36:2636–2632, 1976; M. Hitchcock, J. of Immunology, 118, 578–583, 1977).

This new method of topical treatment of skin and mucosal inflammation is based on inventor's experimental studies using adequate external application of cyclic AMP or it's derivatives in different experimental models of inflammation.

SUMMARY OF THE INVENTION

The invention relates to compositions for the treatment and prevention of skin conditions, eye and mucosal inflammation on humans and animals. This invention may be used to treat or prevent irritation of skin or eye or mucosa of humans and animals such as dogs and cats especially, but not exclusively, by external, topical application.

This invention may be used to treat inflammation and alleviate skin conditions such as sun and weather induced damages, skin disorders producing swelling (edema), redness, irritation, itching allergic reactions such as those produced by chemical agents, scalding, poison oak (dermatitis venenata) or burns and other imflammatory skin reactions of bacterial or fungal origin or produced by ultra-violet or infra-red irradiation. The composition may be used both in a curing function as well as a prophylactic function in case of irritation of skin, mucosa or eye.

According to this invention, there is provided compositions for the treatment or prevention of skin or mucosal conditions comprising, in a suitable pharmaceutical carrier, a compound of the following general formula.

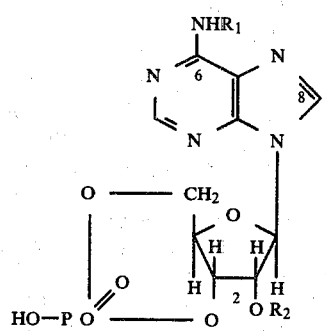

wherein $R_1$ and $R_2$, either are both a butyryl radical or one stands for a hydrogen atom and the other for a butyryl radical or both are hydrogen atom; this compound may be used as such or in the form of any pharmaceutically acceptable salt of the same.

The compounds of the general formula are 3', 5' adenosine monophosphate of cAMP derivatives.

The compositions prepared with these compounds have been shown also to decrease the skin histamin level. These compositions, when applied in pharmaceutically active amounts 1 to 3 times daily, decrease edema arising from scalds or burns, inflammation produced by chemical compounds or organic agents, and improve or prevent itching, redness, swelling, which are caused by scalding, burning or various skin mucosal or eye irritations.

The compositions prepared with these compounds in form of solution or ointment is useful for treatment of prevention of acute eye inflammation produced by foreign bodies, chemicals or burns. The composition with these compounds can be used especially topically for treatment of different kinds of inflammatory processuss of skin, mucosa of ear, throat and mouth and rectal and genital mucosa.

The cAMP derivatives may be made as set out in publications of the inventors (Posternak et al., Bioch. Bioph., Acta 65, 558, 1962, and Cehovic et al., Adv. Cyclic Nucleotides Res., vol. 1, 521, 1972, Raven Press, N.Y.).

Conveniently the compositions are adapted for administration in the form of creams, lotions or sprays, but may also be adapted for subcutaneous intraperitoneal intramuscular or intravenous administration. A pharmaceutically effective amount of the active cAMP ingredient may be admixed, together with phosphodiesterase inhibitor as desired and with a non-toxic carrier suitable for human external use. For example, suitable carriers include combinations of petroleum waxes, sterin, glycerol, lanoline, sesame oil, lanatte wax or propylene glycol.

The effective amount of the selected compound according to the invention may vary with the ingredient selected, any phosphodiesterase inhibitor used, and the severity of the inflammation. Generally, it should be used in concentration of 0.01 to 1% by weight.

The preferred method of application is once, twice or three times daily using enough of the formulation to lightly cover the area to be treated. In the case of different kinds of inflammation of the skin or mucosa, it is important to apply the cream as soon as possible after the appearance of inflammation and to repeat the cream application 2 to 3 hours later. For persons suffering from allergic reactions a preventive topical application of the cream on the skin or in the eye is recommended 2 to 3 hours before exposure to chemical or biological substances which are suspected to produce an allergic reaction.

Improved results are obtained if the cream or the lotion is applied 1 to 2 hours before exposure to sunshine or unfavourable weather conditions. In case of eye irritation produced by foreign bodies or chemicals or burns or irradiation, the preferred method is the treatment by irrigation of the eye and consecutive frequent instillations or applications of active compound in form of ointment or cream.

For experimental studies on eye inflammation, the active compound was diluted physiological solution (NaCl 0.9%) and ph adjusted at 7.3.

Examples 1 to 4 illustrate various formulations (not limitary) for dermatological use, containing a variety of active ingredients:

| Example 1 | Percentage | Example 2 | Percentage |
|---|---|---|---|
| Spermaceti | 13.0 | Beeswax | 17.20 |
| Beeswax | 12.0 | Mineral oil (65/75) | 50.00 |
| Almond oil | 55.0 | | |
| | | Borax | 0.80 |
| Borax | 0.5 | | |
| | | Distilled water | 32.00 |
| Rose Water | 5.0 | | |
| | | N-6 Monobutyryl | |
| Distilled Water | 14.0 | cyclic AMP | 0.01 |
| Rose oil | 0.5 | | |
| Dibutyryl cAMP | 0.01 | | |
| Example 3 | Percentage | Example 4 | Percentage |
| Mineral oil | 50.0 | Stearic acid | 15.0 |
| Beeswax | 7.4 | Lanolin anhydrons | 4.0 |
| Tween 40 | 2.0 | Beeswax | 2.0 |
| Arlaced 1726 | 8.0 | Mineral oil | 23.0 |
| Distilled water | 32.58 | Tween 85 | 1.0 |
| 2'-O monobutyrylcyclic AMP | 0.02 | Arlacel 85 | 1.0 |
| | | Sorbitol | 11.5 |
| | | Distilled water | 42.0 |
| | | Aminophillin | 0.4 |
| | | 3',5'adénosine cyclic monophosphate | 0.1 |

I—Croton oil edema study on mice

Tests were performed on mice for reducing inflammation in Mouse ear edema produced by croton oil (test of Tonelli and all, Endocrinology, 1965, 77, 625–634). This test is a standard anti-inflammatory animal test. Cream base (placebo and not according to the invention) referred in Tables 1, 2, 3, 4 and 6 consists of the following composition (for 1 kg):
Butylhydroxy anisol: 0.1 gr
Cetylic alcohol: 18.0 gr
Stearic acid: 120.0 gr
Glycerol monostearate: 54.0 gr
Glycerin (codex): 120 ml
Triethylamine: 12 ml
Perhydrosqualen: 60 ml
Water: 600 ml
Sodium methyl paraoxybenzoate: 1.2 gr
Collagen lauroyl: 12 ml
Methyl paraoxybenzoate: 2.4 gr
Propyl paraoxybenzoate: 0.4 gr
Ethyl paraoxybenzoate: 0.2 gr
Butyl paraoxybenzoate: 0.2 gr
Sodium ethylene diaminetetracetate: 0.8 gr In this test, 64 mice were used. The inflammation was produced by topical ear application of 2% concentration of croton oil with pyridine. Fifteen to twenty minutes after croton application, different creams were topically applied on the mouse ear. Two hours after, ear sections (dermal punch) were taken, weighed and compared with the control group (I), with the group without treatment (A) and with group (B) treated with the cream base B.

Table 1 shows clearly that cream base (B) produces a little (not statistically significant) decrease in weight of mouse ear section. The cream containing cyclic AMP and theophyllin (C) decreases significantly the inflammation as compared to cream base (B) or no treatment (A) $-25\%$ reduction in weight (C:A) or 40% inhibition of inflammation. The group treated with $N^{6,2'0}$ dibutyryl cyclic AMP (in concentration of 0.01%) showed even a higher decrease of inflammation $-33\%$ reduction in weight (D:A) or 54% on inhibition of inflammation (see Table 1).

Table 1

| | (croton oil edema study) | | | | | | |
|---|---|---|---|---|---|---|---|
| Treatment | N° of animals | Mean ± S.D.[2] | Student test "t" | Signific. | Increase of weight | | Inhibition in 2 h |
| | | | | | mg | % | % |
| Control[1] | 15 | 4.46 ± 0.10 | — | — | — | — | — |
| (A) Without treatment | 10 | 11.50 ± 0.67 | — | — | 7.04 | 158 | — |
| (B) Cream base (Placebo) | 19 | 9.81 ± 0.37 | 2.41 (B:A) | p > 0.01 | 5.35 | 120 | 24 |
| (C) Cream + 0.1% cAMP + 0.4% Theoph. | 20 | 8.67 ± 0.31 | 2.37 (C:B) | 0.01 < p < 0.05 | 4.21 | 94 | 40 |
| (D) Cream + 0.01% DBC | 15 | 7.67 ± 0.24 | 4.53 (D:B) | p < 0.01 | 3.22 | 72 | 54 |
| (E) Cream + 1% hydrocortisone | 9 | 7.53 ± 0.30 | 4.81 (E:B) | p 0.01 | 3.07 | 69 | 56 |

[1]Normal (without irritation with croton oil)
[2]Average weight of mouse ear section in mg ± standard deviation.

II—Scalded ear edema study on mice

The second series of experiments have been made on 62 mice, after a number of preliminary tests, to determine the effectiveness of a topical formulation in inflammation produced by heat or burns. For these experiments a following modification of the original Tonelli test was used. Instead of croton oil, The mice ears were scalded 3 seconds in water bath heated at 55% C, and the scalded section (dermal punch) was taken 1 hour after cream application.

Table 2 shows that a cream base containing 0.1% of cyclic AMP and 0.4% of theophylline (E) decreases significantly (19% decrease of weight as compared to cream base alone), the inflammation produced by scalding. A little but not statistically significantly decrease was obtained with the cream (C) containing only 0.1% of cyclic AMP or only 0.4% of theophylline (D). It demonstrates the activity of this topical cream application on inflammation and the importance of protection of the active ingredient—cyclic AMP against phosphodiestrases present in the tissues by using theophylline to inhibit cAMP hydrolysis (see Table 2).

III—Vascular permeability study on mice

One of the cardinal features of acute imflammation is swelling produced by increased vascular permeability.

In the next series of experiments, in the same scalded mouse ear test, the inhanced vascular permeability was measured quantatively with Evans blue method (Udaka and all, P.S.E.B.M., 1970, 133, 1384–1387).

group treated with cream containing only cyclic AMP, the small decrease was not statistically significant (see Table 3).

IV—Histamine study

Improvement of some allergic reaction in humans using this composition topically could be observed. Allergic reaction produces an increase of the histamine level in the tissue.

The anti-allergic reaction observed on the human skin can be explained by this mechanism of histamine reduction which is supported by the following test. 57 mice were used. The cream was applied on the mouse ear and one hour later a dermal punch was used to remove a circular section of the ear.

The section was immediately weighed and the histamine level tested by fluorometric method with Technicon (Ruff and all., 1967, Nature, London, 214, 279). The Table 2

| Treatment | (scalded ear edema study) | | | | | | |
|---|---|---|---|---|---|---|---|
| | No of mice | Ear sections Means ± S.D.[3] | Student "t" test | Signific. | Increased of weight mg | % | Inhibition % |
| Control[1] | 42 | 4.33 ± 0.12 | — | — | — | — | — |
| (A) Without treatment[2] | 20 | 10.61 ± 0.49 | — | — | 6.28 | 145 | — |
| (B) Cream base (Placebo) | 12 | 10.48 ± 0.41 | — | — | 6.15 | 142 | 0.5 |
| (C) Cream base + 0.1% cAMP | 10 | 9.88 ± 0.30 | 1.1865 (C:B) | $p > 0.1$ | 5.55 | 128 | 10 |
| (D) Cream base + 0.4% Theophy. | 10 | 9.28 ± 0.43 | 1.703 (D:P) | $p > 0.1$ | 4.95 | 114 | 20 |
| (E) Cream base + 0.1% cAMP + 0.45% Theophylline | 10 | 8.51 ± 0.45 | 2.037 (E:B) | $p < 0.05$ | 4.18 | 96 | 33 |

[1]Normal-non scalded ear
[2]Scalded ear without any cream
[3]Average weight of scalded ear section in mg ± standard deviation One hour before scalding, Evans blue (3% solution) was injected intravenously (75 mg/kg) to 20 gr. mice. Fifteen minutes before scalding, the different creams were applied on the mice ears. The dermal punches (16 mm$^2$) were taken one hour after cream application and the ear sections weighed and placed in formamide. After twelve hours of incubation at 50° C., the blue color extracted was measured by a spectrophotometer (Vitatron MPS) at 620 mu. The total amount of due was calculated by means of a standard calibration curve and expressed in mg/mgr, or in mg/cm$^2$.

Table 3 tubulates the results of the test. Fifteen mice, after scalding, were treated with cream base (Placebo) on one ear and with cream base on the other. In the ear treated with cyclic AMP and theophylline, Evans blue decreased (−18% by weight or −24: by surface). In the test was conducted by a laboratory on a blind basis, that is the technician did not known which test formulation was the control and which formulation contained the active ingredients. The average histamine concentrations (μg/mgr.) of the treated ears were compared against the control and a statistical analysis of the results were obtained. Table 4 tabulates the results of the test.

Table 4 shows that the cream base alone produced a very small (5%) but not significant decrease in histamine level in the skin. The cream with theophylline produced no significant change in histamine level (1.2%). The cream with cyclic AMP produced a small but not significant decrease in the histamine level (10%). The cream with cyclic AMP and theophylline produced a statistically significant decrease (20%) of histamine level in the skin (see Table 4).

Table 3

| Treatment | N of mice | Evans Blue ng/mgr. | % of reduction of E.B. | Student "t" test | Signif. Stat. | Evans Blue in ng/mm2 | % of decr. | Student "t" test | Signif. Stat. |
|---|---|---|---|---|---|---|---|---|---|
| Base cream (Placebo) | 15 | 1.267 ± 0.403 | — | — | — | 0.956 ± 0.284 | — | — | — |
| Cream + cAMP 0.1% +Theoph. 0.4% | 15 | 1.045 ± 0.265 | 18 | 1.779 | $p > 0.05$ | 0.728 ± 0.218 | 24 | 2.460 | $0.01 < p < 0.05$ |
| Cream + cAMP (0.1%) | 5 | 1.129 ± 0.372 | 11 | 0.802 | $p > 0.10$ | 0.803 ± 0.214 | 16 | 1.326 | $p > 0.10$ |

Table 4

| Treatment | (Histamine study) | | | | |
|---|---|---|---|---|---|
| | No of mice | Mean ng/mg ± S.D.[1] | Student "t" test | Significance | % of controls |
| (A) Control (without cream) | 10 | 135.15 ± 9.6 | — | — | — |
| (B) Placebo (cream base) | 12 | 128.30 ± 5.7 | n.s. | n.s. | 95.0 |
| (C) Theoph. (cream + 0.4% of theoph.) | 10 | 133.58 ± 7.3 | n.s. | n.s. | 98.8 |

Table 4-continued

| | (Histamine study) | | | | |
|---|---|---|---|---|---|
| Treatment | No of mice | Mean ng/mg + S.D.[(1)] | Student "t" test | Significance | % of controls |
| (D) cAMP (cream + 0.1% cAMP) | 10 | 121.64 ± 4.1 | 1.2878 | p > 0.5 | 90.0 |
| (E) cAMP + Theoph. (0.1% + 0.4% | 15 | 108.70 ± 3.8 | 2.9127 (E:A) 2.9597 (E:B) | p < 0.01 | 80.5 |

[(1)]Means ± S.D. - Average of histamine ng/mgr. of ear section.

V—Croton oil edema study with HSA-$^{125}$I on mice

For better estimation and quantification of the degree of inflammation another series of study was performed with a new method using radiolabelled human serum albumin (HSA-$^{125}$I).

This method is based on the measurement of the increased radioactivity in the inflamed tissue due to the increased exudation of blood proteins in the tissue during acute inflammation.

Cream base referred as placebo consists of the same composition described previously.

Mice are injected i.v. (intravenously) in their tail's vein with iodine$^{125}$ labelled serum albumin at a dose corresponding to 0.5 to 1 μc per animal; one of the ears is treated for inducing an irritation while the other is kept as control. Two hours later a sample of the irritated portion of the treated ear, as well as a comparable sample of the control ear are taken (by dermal punch) and weighed and 0.05 ml of blood are taken by infraorbital punction. The radioactivity of these three samples is then measured by a gamma counter and expressed in counts per minute and per mg for the tissues and in percentage with respect to blood radioactivity. For a non irritated tissue the radioactivity is of about 10% of blood radioactivity; for an irritated tissue, the radioactivity is generally over 110% of the blood one.

By using an appropriate number of mice groups, i.e. for instance, one for control (irritation + topical application of placebo cream), one for each anti-inflammatory preparation to be studied and at least one for a reference anti-inflammatory composition, a very acute and reliable determination of the activity of the preparations of the inventions may be obtained.

For this determination, a first series of three experimentations has been undertaken.

In the first experiment of this series, 26 mice were used. The inflammation was produced by topical ear application of 2% concentration of croton oil with pyridine.

Fifteen to twenty minutes after croton application, different creams were topically applied on the mouse ear. One hour after, ear sections (or dermal punches) were taken, weighed counted in gamma counter and compared with the control group.

Table 5 shows clearly that the cream containing cyclic AMP and theopylline (b) decreases significantly the inflammation as compared to no treatment (a). Significant reduction in weight is observed (as described in previous application) parallely with a significant decrease of radioactivity.

Table 5

| Treatment (right ear) | Blood cpm/mg | Left ear (Control) | | | Right ear (croton oil) | | | Weight inc. % | (R-L)[(3)] Δ% |
|---|---|---|---|---|---|---|---|---|---|
| | | Weight (mg) | cpm/mg | % to blood | Weight (mg) | cpm/mg | % to blood | | |
| (a) None  /11/[(4)] | 551±150[(1)] | 4.22±0.55[(2)] | 63±24 | 11.4±2.4 | 9.77±1.22 | 644±215 | 116.8±18.6* | 131 | 105.4 |
| (b) CAMP (0.1%) + Theoph.  /5/ (0.4%) | 627±72 | 4.15±0.60 | 64±12 | 10.23±1.02 | 6.12±0.93 | 486±164 | 78±29 (5)* | 47 | 68 |
| (c) DBC (0.01%)  /5/ | 654±59 | 3.79±0.49 | 63±14 | 9.62±2.33 | 5.04±0.90 | 384±67 | 59±9.35 (5)* | 33 | 49 |
| (d) Hydrocortisone (1%)  /5/ | 685±77 | 3.92±0.31 | 85±10 | 12.6±2.0 | 5.99±0.87 | 487±152 | 70±15.5 (5)** | 53 | 57 |

[(1)]Count per minute per mg. Mean ± standard deviation
[(2)]Weight in mg. Mean ± standard deviation
[(3)]Δ%, difference between percentages to blood radioactivity of right ear and left ear.
[(4)] /.../: number of mice/group
[(5)]*: p < 0.05
**: p < 0.01

The group treated with N$^6$, 2'-O dibutyryl cyclic AMP or DBC, (c) (in concentration of 0.01%) showed even a higher anti-inflammatory effect as evidenced by the decrease of serum albumin exsuded in the tissues and decrease in weight with respect to irritated non treated tissues. The similar results obtained with hydrocortisone at 1% showed that the DBC is 100 times more active.

The second experiment has been made on 30 mice and instead of punches, the total ears were cut.

Table 6 shows that cream base or placebo has no effect. The cream containing only 0.1% of cyclic AMP and 0.4% of theophylline (c) produces 26% protection against inflammation. DBC at 0.01% (d) produces 40 M of protection. Similar protection is obtained by hydrocortisone at 1% (e) or by phenylbutasone at 5% (f). This result proves the activity of this topical cream application on inflammation and the importance of protection of the active ingredient (DBC is 100 times more active than hydrocortisone and about 500 times more active than phenylbutasone).

In the Table 7 are summarized additional results on 18 mice. Two different concentrations were used (0.005 and 0.01%). At 0.01% DBC (c) induces the same inhibition as in Table 6 (40%) and lower dose (0.005%) of the same (b), induces a lower protection (32%).

In male albino rats (300×400 gr.), after anaesthesy with Pentobarbital (i.v.), the experimental eye irritation was produced by instillation of a drop of mustard oil. The rats received previously 0.5–1 µc/100 gr. of human serum albumin labelled with $^{125}I$ (HSA-$^{125}I$) in the vein of the penis. Irritated eyes were treated by instillation (1 minute) of 0.025 ml of different solutions. After one hour, the eyelids were exercised, weighed and counted in gamma counter samples of blood were taken by infra orbital punction and counted. Non-irritated eyelids in these conditions showed a radioactivity corresponding to 10% of the blood radioactivity. Irritated eyelids radioactivity reached the blood radioactivity level (103%). The treatment with DBC at 0.02% decreased Table 6

| Treatment | N° of mice | Blood cpm/mg | Left ear (Control) cpm/mg | % to Blood | Right ear (Croton-oil) cpm/mg | % to Blood | (3) Δ% | % of inhibition | Signification |
|---|---|---|---|---|---|---|---|---|---|
| (a) None | 5 | (1) 435 ± 65 | 42.1 ± 10 | 9.65 | 488 ± 142 | 118 | 101 ± 17 | — | — |
| (b) Placebo (cream base) | 5 | 419 ± 98 | 40.0 ± 8 | 9.53 | 463 ± 91 | 112 | 102 ± 18 | 1.5 | t = 0.14 n.s. b:a |
| (c) cAMP (0.1%) + Theoph. (0.4%) | 5 | 481 ± 68 | 42.7 ± 6 | 9.06 | 410 ± 47 | 85.6 | 76 ± 2.7 (5) * | 26.0 | t = 3.07 c:a |
| (d) DBC (0.01%) | 5 | 467 ± 55 | 43.8 ± 14 | 9.30 | 334 ± 87 | 71.0 | 61 ± 11 (5) ** | 40.0 | t = 4.17 d:a |
| (e) Hydrocortisone (1%) | 5 | 484 ± 54 | 47.5 ± 8 | 9.70 | 383 ± 49 | 78.4 | 69 ± 12 (5) * | 33.0 | t = 3.29 e:a |
| (f) Phenylbutasone (5%) | 5 | 522 ± 48 | 51.4 ± 12 | 9.99 | 359 ± 45 | 69.0 | 59 ± 5.4 (5) ** | 43.0 | t = 5.06 f:a |

(1), (3) & (5): of Table 5

Table 7

| Treatment | N° of mice | Blood cpm/mg | Left ear (control) cpm/mg | % to Blood | Right ear (croton oil) cpm/mg | % to Blood | (3) Δ % | % of inhibition | Signification (t) |
|---|---|---|---|---|---|---|---|---|---|
| (a) None | 4 | (1) 223 ± 9 | 20.6 ± 3 | 9.22 | 257.4 ± 19 | 115.5 | 106.2 ± 11 | — | — |
| (b) DCB (0.005%) | 4 | 202 ± 39 | 25.5 ± 10 | 12.3 | 163.9 ± 13 | 82.8 | 70.4 ± 12 (5) ** | 32 | t = 4.24 p < 0.01 b:a |
| (c) DBC (0.01%) | 10 | 230 ± 23 | 25.5 ± 10 | 11.1 | 176.3 ± 46 | 76.2 | 65.1 ± 20 (5) ** | 40 | t = 3.79 p < 0.01 c:a |

(1),(3) & (5) : cf Table 5

VI—Eye irritation study on rabbits and rats

An another series of experiments has been made, in order to show the utility of these compounds for treatment of eye inflammation.

In this series, the first experiment was on rabbits. The activity of DBC was studied on Albino Belge rabbits (1 to 1.5 kg) by a technique derived from that one of F.D.A. Food and Drug Administration, 1965; Illustrated guide for grading eye irritation by hazardous subs.); the application of a solution containing 0.02% of DBC has the same effect, on the irritation, as commercial hydrocortisone at 1%. For a better quantification of this anti-inflammatory activity, another method, based on the differential measurement of extravasation of serum albumin, was used. It is described with more details in the following experiment.

The second experiment of this series used rats instead of rabbits, and was undertaken as follows.

that radioactivity to 50% similarly to that of hydrocortisone at 1%—(See Table 8).

The measurement of the radioactivity of irritated tissue corresponds to albumin extravasation due to inflammation, as previously reported.

Table 8

| (*) Weight (mg) | cpm (total) | cpm/ mg | (**) % to Blood | Weight (mg) | cpm (total) | cpm/ mg | % to blood |
|---|---|---|---|---|---|---|---|
| A. Non irritated eye | | | | B. Irritated eye (Mustard) without treatment | | | |
| 28 | 407 | 14.5 | 14.9 | 35.2 | 3 287 | 93.4 | 124.5 |
| 40 | 425 | 10.6 | 10.8 | 44.3 | 3 216 | 72.6 | 96.8 |
| 49 | 430 | 8.8 | 11.4 | 41 | 3 137 | 76.5 | 109.3 |
| 38.6 | 313 | 8.1 | 10.5 | 47 | 3 411 | 72.6 | 113.6 |
| 48 | 494 | 10.3 | 13.3 | 65 | 3 966 | 61 | 78.8 |
| 41 | 324 | 7.9 | 10.2 | 94 | 7 091 | 75.4 | 97.5 |
| Mean (% to blood) | | | 11.85 | Mean (% to blood) | | | 103.41 |

Table 8-continued

| (*) Weight (mg) | cpm (total) | cpm/mg | (**) % to Blood | Weight (mg) | cpm (total) | cpm/mg | % to blood |
|---|---|---|---|---|---|---|---|
| C. Irritated eye (Mustard) + DBC - 0.02% | | | | D. Irritated eye + hydrocortisone 1% | | | |
| 66 | 2 526 | 38.3 | 49.7 | 62 | 3 351 | 54.1 | 55.3 |
| 68.5 | 3 435 | 50.1 | 65.1 | 60 | 2 589 | 43.2 | 44.2 |
| 81 | 3 707 | 45.7 | 60.4 | 53 | 2 588 | 48.8 | 44 |
| 70 | 2 590 | 37 | 48 | 56 | 3 782 | 67.5 | 51.9 |
| 52 | 2 091 | 40.2 | 40.2 | 78 | 4 787 | 61.3 | 63.2 |
| 76 | 2 784 | 36.6 | 36.6 | 68 | 3 981 | 58.5 | 59.8 |
| Mean (% to blood) | | | 50.0 | Mean (% to blood) | | | 53.1 |

Legend of Table 8
(*): weight of palpebra (eyelids)
(**): radioactivity of eyelids expressed in percentage to the blood radioactivity.
cpm: count per minute
cpm/mg: count per minute and per milligram of tissue.
The mean percentage of tissue activity to the blood radioactivity in non-irritated tissue (group A) is: 11.85%
In irritated eyelids, this mean (group B) is: 103.41%
In irritated tissue treated with DBC at 0.02%, the mean percentage (group C) is: 50.0%.
In irritated tissue treated with hydrocortisone at 1%, this mean (group D) is: 53.3%.
In the case of hydrocortisone at 1%, the protection is 54.9 and in case of DBC at 0.02% the protection is 58.3%.
According to these results, the protection obtained with 0.02% of DBC is equal or superior to that obtained with 1% of hydrocortisone.

VII—Irradiation study on rats

In order to bring a supplementary proof of the anti-inflammatory activity of the compositions of the invention on different type of inflammation, an another kind of experiment has been undertaken, using a different irritating agent and a different tissue zone.

In this last experiment, the irritation was provoked by UV+IR exposition of the belly skin of rats (male albino rats 300–400 g). After anaesthesy by Pentobarbital, ten rats were injected (in penis vein) with, per 100 g of weight, 0.5 µg of iodine $^{125}$ labelled serum albumin and 100 µg of Evans blue. The belly skin of rats is shaved and covered by a plastic screen bearing 4 holes (diameter 1.2 cm) and the skin appearing through the holes is exposed to a U.V.+I.R. source (Babyliss UV+I.R. 400 W) for 60 seconds; the cream with 0.02% of DBC is applied on two of the zones of each rat whereas the two remaining zones are not treated.

One hour later, a sample of blood (0.1 ml) is taken by infra-orbital punction, the four exposed zones of each rat are taken (these zones are coloured in blue due to the concentration of this agent in irritated tissues) and also four similar zones but in a portion of belly skin not exposed to the irradiation. All the samples are weighed and counted (gamma counter). Average value for count per minute per mg for blood is 121.75±2.75).

The average values for the various kind of samples are reported on the following table, with the same conventions as in preceding tables (See Table 9).

Table 9

| Blood | Non irradiated skin | | Irradiated skin (without treatment) | | Irradiated Skin (DBC - 0.01%) | |
|---|---|---|---|---|---|---|
| cpm/mgr. | cpm/mgr. | % to blood | cpm/mgr. | % to blood | cpm/mgr. | % to blood |
| 105 ± 2 | 11.8 ± 0.6 | 10.9 ± 0.5 | 73.1 ± 16 | 69.6 | 58.6 ± 10 | 55.8 |
| 48 ± 1 | 6.4 ± 0.1 | 13.1 ± 0.2 | 36.1 ± 1 | 75.2 | 28.2 ± 2 | 58.7 |
| 127 ± 4 | 15.5 ± 4 | 11.9 ± 2 | 93.9 ± 2 | 73.9 | 53.1 ± 4 | 41.8 |
| 207 ± 4 | 21.4 ± 6 | 10.3 ± 4 | 185.6 ± 8 | 89.7 | 106.1 ± 11 | 51.2 |
| 109 ± 3 | 7.3 ± 0.1 | 6.7 ± 0.1 | 122.5 ± 13 | 112.4 | 84 ± 19 | 77.0 |
| 126 ± 3 | 9.9 ± 0.5 | 7.8 ± 0.5 | 107.9 ± 16 | 85.6 | 75 ± 10 | 59.5 |
| Mean (% to blood) | | 10.1% | | 84.4% | | 57.3% |

VIII—Prevention study with irradiation

Using the same previously described method of irritation produced by exposure to irradiation (Babyliss UV+IR 400 W) the preventive action of the composition was studies.

Fifteen minutes before irradiation and the injection of radiolabelled serum albumin, the right side of shaved belly skin of rats was pretreated with cream containing DBC at 0.02%.

After irradiation, the corresponding portions of skin were excised and counted and calculated as previously mentioned.

The following Table 10 summarizes the results. The pretreatment with DBC produced an important decrease in radioactivity as compared to non pretreated skin (60–98%). The calculated protection is: p=40%.

Table 10

| Non irradiated skin | | Irradiated skin (U.V. + I.R.) | | Irradiated skin pretreated with DBC 0.02% | |
|---|---|---|---|---|---|
| cpm/mg | % to blood | cpm/mg | % to blood | cpm/mg | % to blood |
| 8,47 | 5,7% | 156,0 | 106,0% | 72,3 | 52,6% |
| 7,36 | 5,0% | 184,3 | 125,0% | 105,8 | 72,0% |
| 7,19 | 4,3% | 101,1 | 60,5% | 97,4 | 58,3% |
| 6,74 | 4,0% | 166,8 | 100,0% | 90,2 | 54,0% |
| 5,93 | 5,1% | 108,8 | 93,8% | 50,4 | 43,4% |
| 5,80 | 5,0% | 117,5 | 101,3% | 96,0 | 82,7% |
| Mean (in % to blood) | 4,86% | | 97,7% | | 60,5% |

IX—Observation on human volunteers

A serious improvement was observed also on two children (6 and 8 years old) bit by bees, after topical application of a cream described as "C" in Table 6 (with cAMP at 0.1% and theophyllin at 0.4%).

A quick disappearance of itching and a rapid decrease of redness was observed on 3 young boys (8–14 years old) and 2 girls (16 and 18 years old) with serious sunburn after application of the same cream ("C" in table 6).

According to the declaration of two volunteers suffering of allergic reaction to chemicals, prophylactic application of composition with DBC in solution of 0.2% (see group C in table 8) 2×5 drops in eye, reduced quite completely the irritation usually caused by ether evaporation.

We claim:

1. Composition for treatment of inflammation of skin, eye and mucosa in animals especially, but not exclusively, by external topical application comprising an effective amount of cyclic nucleotide having the following structural formula:

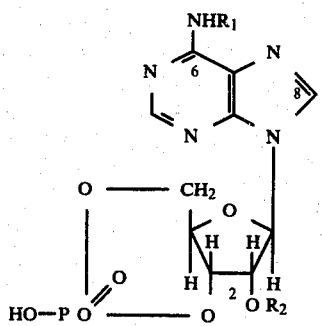

wherein $R_1$ and $R_2$, either are both a butyryl radical or one stands for a hydrogen atom and the other for a butyryl radical any pharmaceutically acceptable salt of the same.

2. The method of treating inflammation of skin, eye and mucosa in animals comprising the administration in a pharmaceutically acceptable carrier of an effective amount of a composition having the following structural formula:

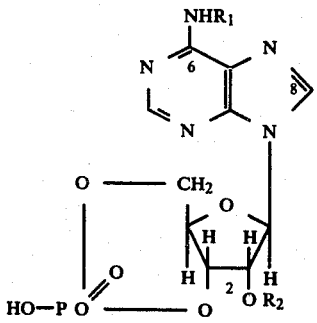

wherein $R_1$ and $R_2$ are both butyryl radicals, or one is a hydrogen atom and the other is a butyryl radical or a pharmaceutically acceptable salt of the same.

3. The method of reducing the histamine level in animals comprising the administration in a pharmaceutically acceptable carrier of an effective amount of a composition having the following structural formula:

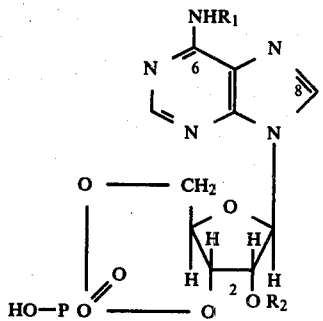

wherein $R_1$ and $R_2$ are both butyryl radicals, or one is a hydrogen atom and the other is a butyryl radical or a pharmaceutically acceptable salt of the same.

4. The method of treatment to protect against inflammation of skin, eye and mucosa comprising the administration in a pharmaceutically acceptable carrier of an effective amount of a composition having the following structural formula:

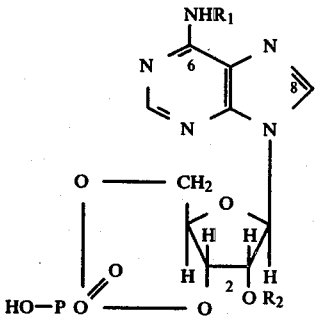

wherein $R_1$ and $R_2$ are both butyryl radicals, or one is a hydrogen atom and the other is a butyryl radical or a pharmaceutically acceptable salt of the same.

* * * * *

UNITED STATES PATENT AND TRADEMARK OFFICE
CERTIFICATE OF CORRECTION

PATENT NO. : 4,208,406              Page 1 of 3
DATED     : June 17, 1980
INVENTOR(S) : Eugène Lapinet, Georges Cehovic, Théodore Posternak It is certified that error appears in the above—identified patent and that said Letters Patent are hereby corrected as shown below:

In the middle of the Abstract, at the top of column 2 and in claims 1, 2, 3 and 4, the structural formula is changed to appear:

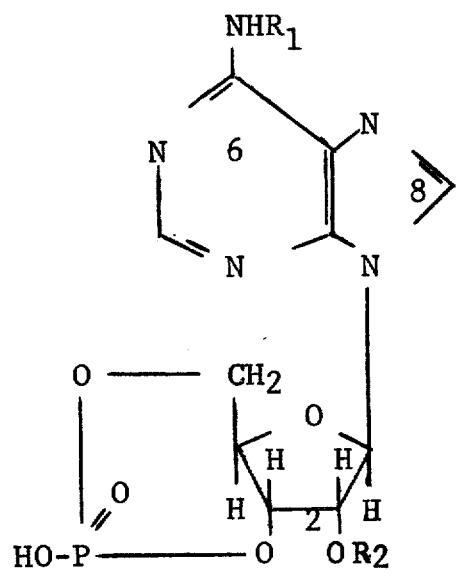

UNITED STATES PATENT AND TRADEMARK OFFICE
CERTIFICATE OF CORRECTION

PATENT NO. : 4,208,406
DATED : June 17, 1980
INVENTOR(S) : Eugène Lapinet, Georges Cehovic, Théodore Posternak It is certified that error appears in the above-identified patent and that said Letters Patent are hereby corrected as shown below:

Column 3, line 14, after "diluted" insert --in--.

Column 5, Table 2, Treatment (D), column Student "t" test, change "(D:P)" to -- (D:B)--.

Column 5, Table 2, Treatment (E), change "0.45%" to --0.4%--.

Column 5, line 42, change "due" to --die--.

Column 7, Table 5, Treatment (right ear) column, under (a) change "(4)" to --4)--.

Column 7, Table 5, Treatment (right ear) column, under (b) change "CAMP" to --cAMP--.

Column 7, Table 5, Treatment (right ear) column, under (c) % to blood column, change "(5)*" to --(5)**--.

UNITED STATES PATENT AND TRADEMARK OFFICE
CERTIFICATE OF CORRECTION

PATENT NO. : 4,208,406

DATED : June 17, 1980

INVENTOR(S) : Eugène Lapinet, Georges Cehovic, Théodore Posternak

It is certified that error appears in the above-identified patent and that said Letters Patent are hereby corrected as shown below:

Column 9, Table 6, footnote of Treatment column, change "of" to --cf--.

Column 13, line 17, after "radical" insert --or--.

Signed and Sealed this

Twentieth Day of January 1981

[SEAL]

Attest:

RENE D. TEGTMEYER

Attesting Officer

Acting Commissioner of Patents and Trademarks